United States Patent [19]

Worrell

[11] 4,257,852
[45] Mar. 24, 1981

[54] DISTILLATION OF AQUEOUS TERTIARY BUTYL HYDROPEROXIDE

[75] Inventor: G. Richard Worrell, Media, Pa.

[73] Assignee: Atlantic Richfield Company, Los Angeles, Calif.

[21] Appl. No.: 3,311

[22] Filed: Jan. 15, 1979

[51] Int. Cl.$^3$ .............................................. B01D 3/32
[52] U.S. Cl. ...................................... 203/99; 203/71; 203/86; 203/DIG. 22; 202/154; 202/158; 202/267 R; 202/270; 220/88 A; 568/576
[58] Field of Search ............ 568/576, 562; 220/88 A; 48/192; 431/354; 55/DIG. 28; 202/182, 158, 154, 235, 267–270, 197; 203/DIG. 22, 7, 99, 89, 86, 40, 78, 80, 84, 71, 73; 196/155

[56] References Cited

U.S. PATENT DOCUMENTS

| | | | |
|---|---|---|---|
| 1,974,091 | 9/1934 | Wortmann | 220/88 A |
| 2,383,919 | 8/1945 | Rust | 568/576 |
| 2,520,870 | 8/1950 | Wood et al. | 202/197 |
| 2,990,341 | 6/1961 | Graybill | 203/86 |
| 3,060,105 | 10/1962 | Müller | 203/86 |
| 3,079,242 | 2/1963 | Glasgow | 48/192 |
| 3,106,515 | 10/1963 | Williams | 203/86 |
| 3,864,216 | 2/1975 | Worrell et al. | 568/576 |

Primary Examiner—Wilbur L. Bascomb, Jr.
Attorney, Agent, or Firm—John R. Ewbank

[57] ABSTRACT

Hazards are dealt with by appropriate placement of high heat capacity flame arrestor packings at suitable zones in the flow of the process streams comprising vapors of flammable mixture containing water and more than 10 mol % tertiary butyl hydroperoxide (conveniently designated as TBHP). Stainless steel mesh or other corrosion resistant high heat capacity packing is inserted in the lower portion of the first distillation zone, from which all components more volatile than dilute aqueous TBHP are removed. Suitable packing is also inserted into the upper portion of the second distillation zone, whereby a flammable mixture containing more than 10 mol % TBHP, is distilled without allowing a large plenum filled with flammable vapor. The vapor line between the top of such distillation zone and a condensation zone features a plurality of flame arrestors (e.g. a cylinder having a length and diameter of at least twice the effective diameter of the vapor line, and filled with corrosion resistant high heat capacity packing having a density greater than about 0.08 g/cc.) The spacing apart of such flame arrestors is from about 15 to 30 times the effective diameter of such vapor line. If any combustion starts in such vapor line, it is constrained between a pair of flame arrestors, thus protecting the purification system before extensive damage occurs. For a given size distillation zone, the aqueous TBHP can be distilled at a faster rate by such use of flame arrestors than by previous distillation arrangements.

4 Claims, 1 Drawing Figure

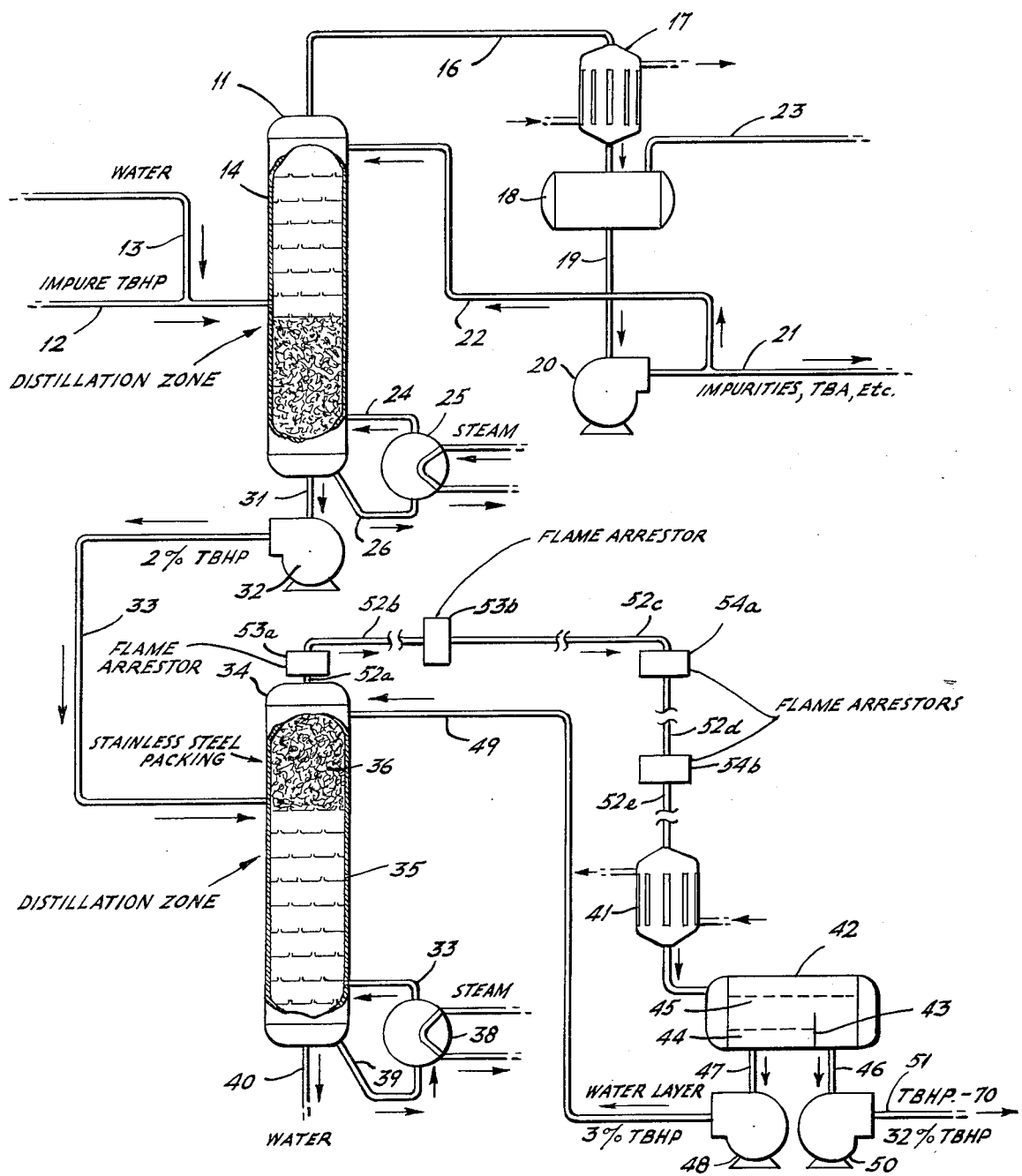

DISTILLATION OF AQUEOUS TERTIARY BUTYL HYDROPEROXIDE

FIELD OF INVENTION

This invention relates to the distillation of aqueous tertiary butyl hydroperoxide and particularly to the coping with the hazard of inadvertent combustion of vapors comprising tertiary butyl hydroperoxide and water.

PRIOR ART

Worrell et al U.S. Pat. No. 3,864,216 describes a distillation of aqueous impure tertiary butyl hydroperoxide. The more volatilizable components are removed from the feed material in a first stage distillation system in which an appropriate inert gas is recirculated there through, whereby the vapors are consistently outside the range of dangerous composition. A purified aqueous TBHP stream is produced safely.

Harvey U.S. Pat. No. 3,449,217 describes a distillation of aqueous TBHP in which the aqueous TBHP "overhead is condensed and phase separated into an upper phase containing 70% by weight TBHP and a lower phase containing 15 weight % TBHP which could, if desired, be recycled."

Rust, U.S. Pat. No. 2,383,919 describes a distillation process aimed at recovering di (tertiary butyl) peroxide.

Frank et al U.S. Pat. No. 2,706,708 describes a distillation process aimed at preparing cumene hydroperoxide.

Herzog, U.S. Pat. No. 3,427,229, employs a refluxing agent in the distillation of TBHP.

Although the prior art technologists struggled with the problems relating to the distillation of aqueous TBHP, there was a continuing search for an appropriate process for distilling aqueous TBHP so that the capital cost for a given capacity could be advantageously low.

SUMMARY OF THE INVENTION

In accordance with the present invention aqueous TBHP is distilled in distillation zones and vapor flow zones which includes appropriate packing, adapted to function as a flame arrestor in the event of any accidental conflagration in a limited zone. Such packing should be corrosion resistant, of high heat capacity, and provide a large surface per unit volume. The packing can be described as a bed of particles which provide a large volume of interstices amongst the particles, whereby the pressure drop of a vapor stream through such bed of particles is sufficiently small to be acceptable for the particular engineering situation. Stainless steel mesh and alumina saddles exemplify suitable particles, but metal Raschig rings and ceramic (e.g. kaolin) balls and related inert packings should be suitable if the engineering modifications were made to obtain heat capacities, percentage of volume of interstices, and surface areas equivalent to those of stainless steel mesh packing. Ordinarily the packing density is within a range from about 5 to about 50 pounds per cubic feet in order to achieve engineering objectives such as low pressure drop and high surface. By positioning flame arrestor structures at appropriately close intervals in the zones in which they are needed, any conflagration is restricted to a small potion of the total distillation apparatus, generally to the zone between two flame arrestors. In the event that a conflagration starts, the fire does not spread, but is confined to the zone between two flame arrestors. Such an accidental fire can be brought under control by temporarily shutting down the distillation unit and cooling the flame arrestors. By designing the distillation system so that the accidental conflagrations are restricted to a confined zone, it is feasible to design and operate a distillation zone of a given size (tower diameter and height) for the processing of vapor containing significantly more TBHP than is possible with the same size distillation zone when constrained by the flammability limits. Thus it is feasible to use the present invention for providing a given capacity for production of aqueous TBHP at a lower cost than would otherwise be feasible. Moreover, for a given capacity, both the operating costs and the capital costs are significantly less using the concepts of the present invention.

DESCRIPTION OF DRAWINGS

In the accompanying flow sheet drawing, there is a schematic showing of a distillation system featuring the present invention.

DESCRIPTION OF INVENTION

As shown in the drawing, a distillation system comprises a first distillation zone 11. A feed stock consisting of impure TBHP is supplied through line 12 and is diluted with fresh water or a recycle stream consisting predominantly of water but containing the miscellaneous impurities attributable to recycling, such stream being designated as 13, and merging with the feed stock prior to being fed to a middle portion of the first distillation zone 11. In the distillation zone 11, there are, above the feed stock injection zone a plurality of equilibration systems such as distillation trays 14. However, in at least a portion of the distillation zone 11 below the injection of feed stock 12, the space is filled with high surface area material having a high heat capacity, for example, stainless steel mesh can be packed in the spaces between the trays, or the trays can be removed and the column can be filled with stainless steel packing.

Distillation zone 11 is adapted to remove the components more volatile than a mixture of water and TBHP withdrawn as bottoms. Volatile vapors are withdrawn from the distillation zone 11 through line 16 and directed to a condenser 17 which directs the condensate into a drum 18. The condenser desirably comprises a shell (through which cold water is circulated) and a bundle of small tubes having an internal diameter of less than about an inch, the vapor flowing into the warm zone of such tubes and the condensate being withdrawn from the cool zone of such tubes. Such shell and tube type of condenser functions as an active flame arrestor so long as cold water is circulating and can be distinguished from the passive or dormant flame arrestor which does not require application of energy (e.g. water circulation) for effectiveness. Gaseous impurities are discharged from drum 18 through off-gas line 23. A line 19 directs the condensate from drum 18 through a pump 20 which recycles a portion of the condensate through line 22 while directing a portion of such condensate to a recovery system through line 21. Tertiary butyl alcohol and other by-products boiling below an appropriate control temperature are thus removed from the first distillation zone through line 21. The off-gas line 23 and liquids in line 21 are volatile impurities removed from the TBHP by the first distillation zone.

An aqueous solution of TBHP is withdrawn from a lower portion of distillation column 11 through line 26 and directed through a reboiler 25 to provide a predominantly vapor stream 24 for maintaining the distillation operation in zone 11. Steam can be supplied to heat exchanger 25 for controlling the vaporization of stream 24.

An aqueous stream containing TBHP is directed through line 31 and pump 32 to line 33 as the feed stock for a central portion of a second distillation zone 34. Beneath the point of feed supply, the distillation zone 34 includes a plurality of trays 35 adapted to permit recovery of a significant portion of the TBHP from the stream of water 40 (containing all of the nonvolatile impurities in the impure TBHP of line 12) withdrawn from distillation zone 34. A stream of water 39 is withdrawn from the bottom of distillation zone 34, directed through a heat exchanger 38 to provide a vapor stream 37 for heating distillation zone 34 sufficiently for maintenance of the distillation. The amount of steam directed through heat exchanger 38 is among the controls for managing the distillation in zone 34.

Particular attention is directed to the fact that stainless steel mesh 36 is provided as packing in a suitable zone, such as that near an upper portion of distillation zone 34. If desired, such packing can extend throughout the entire distillation zone 34. Such packing serves not merely to enhance the equilibria between liquid and vapor, but also functions as a flame arrestor in the event of any accidental burning of vapor. By reason of the presence of such flame arrestor in the upper portion of distillation zone 34, it is feasible to control the distillation so that an azeotrope containing about 20 mol % TBHP is withdrawn from the top of the distillation zone 34 through line 52a. In prior art distillation systems, the existence of plenum zones at such portions of the apparatus prompted restriction of the concentration of TBHP to below the flammable level.

Flame arrestors 53a, 53b, 54a and 54b illustrate the concept of installing flame arrestors at locations spaced along the length of vapor line 52 so that no portion of the vapor line extends for an excessive number of effective diameters of the vapor line. The vapor lines customarily are of circular cross section, but if of a different shape, the effective diameter designates the diameter of a cylindrical conduit having an equivalent cross sectional area. Certain advantages accrue from having flame arrestors spaced at about every 15 diameters but it is important that the spacing be not greater than about 30 diameters in accordance with the present invention. Although the drawing happens to show flame arrestors 53a, 53b, 54a and 54b positioned at intermediate locations of vapor lines 52a, 52b etc., it should be recognized that there can be more or less flame arrestors while complying with the requirements of the present invention. If the vapor line is about a 6 inch conduit, then the flame arrestor can have a diameter and length of about 12 inches, or about twice the conduit diameter. It is important that the heat capacity of a passive flame arrestor be sufficient to cool a flame front sufficiently that it does not migrate the full length of the flame arrestor. Hence flame arrestors are often from about 3 to 6 diameters in length instead of said minimum of 2. Moreover, a minimum diameter and length of 6 inches is required by the present invention even when the vapor line is less than 3 inches in effective diameter.

Each such flame arrestor should be packed with high surface area material having a high heat capacity and appropriate resistance to corrosion by impure and concentrated TBHP. For example, a flame arrestor 53a may be packed with stainless steel mesh having a density of at least about 5 lb. per cubic foot. In the event of an accidental fire, any combustion of vapors of TBHP is likely to be confined to a zone between a pair of flame arrestors during the emergency pending shutdown of the distillation of the distillation system. Because of the ease of coping with conflagrations and the likelihood of confining such accidental fires, there is engineering justification for assuming the risks inherent in distilling flammable vapors of TBHP and water. By such assumption of the risk of a confined fire, the routine distillation can be conducted at a higher TBHP concentration, at a lower capital cost, and with lower operating costs.

The condensate from condenser 41 is directed to a decantation vessel 42 in which a baffle 43 permits the separation of a lower layer 44 from an upper layer 45. The lower layer is withdrawn from vessel 42 through line 47 and directed by pump 48 through line 49 to an appropriate upper portion of distillation zone 34. Such recycle stream oftentimes has a composition corresponding approximately to 3 mol % TBHP and about 97 mol % water.

A desired product containing about 32 mol % TBHP is withdrawn through line 46 and pump 50 to a product discharge line 51. Such product contains about 70 weight % TBHP and has been marketed as 70% TBHP as a tank car chemical for more than a year, as produced by distillation systems such as disclosed in Harvey U.S. Pat. No. 3,449,217.

It should be noted that the molecular weight of TBHP is several times the molecular weight of water. Reference can be made to the following table in interpreting various compositions as expressed either as mol % or as weight %.

TABLE

| AQUEOUS TBHP | |
|---|---|
| Mol % TBHP | Weight % TBHP |
| 2 | 9.26 |
| 3 | 13.4 |
| 10 | 35.7 |
| 20 | 55.6 |
| 32 | 70.2 |
| 40 | 76.9 |
| 80 | 95.2 |
| 90 | 97.8 |
| 99 | 99.8 |

The invention, when thought of as a process, can be further clarified as a process for the preparation of an aqueous solution containing about 32 mol percent tertiary butyl hydroperoxide from an impure dilute aqueous system comprising tertiary butyl hydroperoxide which comprises: subjecting said dilute aqueous system comprising tertiary butyl hydroperoxide to separate at least one stream containing volatile impurities, and to separate at least one stream containing impurities less volatile than tertiary butyl hydroperoxide, and to recover the condensate from a flammable vapor stream containing water vapor and more than 10 mol percent tertiary butyl hydroperoxide vapor; subjecting said condensate to decantation to recover an upper layer consisting of about 32 mol percent tertiary butyl hydroperoxide and about 68 mol percent water as the product of the process; coping with the flammability problem by providing flame arrestor devices at each of a plurality of locations subjected to said flammable vapor comprising more than 10 mol percent tertiary butyl hydroperoxide, such flame arrestor devices being positioned in those portions of the distillation zone containing said flammable vapors of a mixture comprising more than 10 mol percent tertiary butyl hydroperoxide and such flame arrestor devices being positioned at locations spaced apart by from about 10 to about thirty effective diameters of vapor lines containing said flammable vapor comprising more than 10 mol percent tertiary butyl hydroperoxide, whereby in the event of an accidental fire, such fire is initially confined to a zone between nearby flame arrestors during an alerting period appropriate for bringing such fire under control, said use of said flame arrestors permitting distillation of a vapor forming a condensate containing a larger concentration of tertiary butyl hydroperoxide than would be attainable from condensate from nonflammable vapors, thereby recovering a given quantity of 3 mol percent tertiary butyl hydroperoxide at both capital costs and operating costs lower than when condensate is obtained only from nonflammable vapors.

The invention, when viewed as featuring apparatus, can be further clarified as a system comprising: at least one distillation apparatus comprising a system for feeding an impure aqueous solution comprising tertiary butyl hydroperoxide to a central portion of a first distillation tower; corrosion resistant packing in a lower portion of said first distillation tower; means for withdrawing an overhead stream from an upper portion of said first distillation tower, for condensing said vapors to provide a condensate for withdrawing uncondensed effluent from said overhead stream for recirculating a portion of said condensate to said first distillation tower, and for withdrawing a portion of said condensate; means for heating appropriate portions of said first distillation tower; means for directing a stream from a lower portion of said first distillation tower to a central portion of a second distillation tower; corrosion resistant packing in an upper portion of said second distillation tower said packing functioning both to promote localized equilibria between liquid and vapor and as a flame suppressor in a zone in which the water vapor concentration is low enough to provide flammable vapors comprising tertiary butyl hydroperoxide; means for withdrawing an aqueous system consisting of water and impurities less volatile than water from a lower portion of said second distillation tower; vapor line means for withdrawing an overhead stream from an upper portion of said second distillation tower; a plurality of flame arrestors in said vapor line means, each flame arrestor being filled with corrosion resistant packing at a density of at least about 5 pounds per cubic foot, and each flame arrestor having an effective length and an effective diameter of at least about six inches and at least twice the effective diameter of said vapor line means, and said flame arrestors being spaced from other flame arrestors a distance corresponding to from about 15 to about 30 effective diameters of said vapor line means, whereby any accidental conflagration of vapor in said line means is constrained between a pair of said flame arrestors during an interval normally sufficient to permit extinction of such conflagration; a condenser for condensing the vapor in said overhead stream from the second distillation tower; decantation means for separating condensate from said second distillation tower into an upper layer and a lower layer; means for recirculating said lower layer from the decantation means to an upper portion of said second distillation tower; and means for withdrawing from the upper layer of said decantation means a stream consisting of about 32 mol percent tertiary butyl hydroperoxide and about 68 mol percent water as the significant valuable product of the distillation process.

Various modifications of the invention are possible without departing from the scope of the present invention and the description of the operation of the system shown in the drawing should be recognized as being merely an illustrative embodiment of the invention.

The invention claimed is:

1. A process for the preparation of an aqueous solution containing about 32 mol percent tertiary butyl hydroperoxide from an impure aqueous system comprising tertiary butyl hydroperoxide which process comprises:

subjecting a stream of said dilute aqueous system comprising tertiary butyl hydroperoxide to a total distillation system for separating at least one stream containing impurities, more volatile than tertiary butyl hydroperoxide and for separating at least one stream containing impurities less volatile than tertiary butyl hydroperoxide, and for recovering from a distillation tower a stream containing $H_2O$ and more than 10 mol percent tertiary butyl hydroperoxide;

subjecting said stream containing $H_2O$ and more than 10% tertiary butyl hydroperoxide to cooling and to decantation to recover an upper layer consisting of about 32 mol percent tertiary butyl hydroperoxide and about 68 mol percent water as the product of the process;

coping with the flammability problem by providing flame arrestor devices at each of a plurality of locations downstream from said distillation tower, which locations are subjected to a stream of flammable vapor comprising $H_2O$ and more than 10 mol percent tertiary butyl hydroperoxide, such flame arrestor devices being positioned in those portions of said downstream locations containing said flammable vapors of a mixture comprising more than 10 mol percent tertiary butyl hydroperoxide and such flame arrestor devices being positioned at locations spaced apart from each other by from about ten to about thirty effective diameters of vapor lines containing said flammable vapor comprising more than 10 mol percent tertiary butyl hydroperoxide, whereby in the event of an accidental fire, such fire is initially confined to a zone between nearby flame arrestors during an alerting period appropriate for bringing such fire under control, said use of said flame arrestors permitting distillation of a vapor forming a condensate containing a larger concentration of tertiary butyl hydroperoxide than would be attainable from condensate from nonflammable vapors, thereby recovering a given quantity of 32 mol percent tertiary butyl hydroperoxide at both capital costs and operating costs lower than when condensate is obtained only from nonflammable vapors.

2. A system comprising:

at least one distillation apparatus comprising a system for feeding an impure aqueous solution comprising tertiary butyl hydroperoxide to a central portion of a first distillation tower;

corrosion-resistant packing in a lower portion of said first distillation tower;

means for withdrawing an overhead stream of vapors from an upper portion of said distillation tower;

means for condensing a portion of said vapors to provide a condensate;

means for withdrawing uncondensed effluent from said overhead stream;

means for recirculating a portion of said condensate to said first distillation tower;

means for withdrawing a portion of said condensate;

means for heating appropriate portions of said first distillation tower;

means for directing a stream from a lower portion of said first distillation tower to a central portion of a second distillation tower;

corrosion-resistant packing in an upper portion of said second distillation tower, said packing functioning both to promote localized equilibria between liquid and vapor and as a flame suppressor in a zone in which the water vapor concentration is low enough to provide flammable vapors comprising tertiary butyl hydroperoxide;

means for withdrawing an aqueous system consisting of water and impurities less volatile than water from a lower portion of said second distillation tower;

vapor line means for withdrawing an overhead stream from an upper portion said second distillation tower;

a plurality of flame arrestors in said vapor line means, each flame arrestor being filled with corrosion-resistant packing at a density of at least about 5 pounds per cubic foot, and each flame arrestor having an effective length and an effective diameter of at least about six inches and at least about twice the effective diameter of said vapor line means, and each of said flame arrestors being spaced from a nearby flame arrestor a distance corresponding to from about 15 to about 30 effective diameters of said vapor line means, whereby any accidental conflagration of vapor in said line means is constrained between a pair of said flame arrestors during an interval normally sufficient to permit extinction of such conflagration;

a condenser for condensing the vapor in said overhead stream from the second distillation tower to prepare a condensate from said second distillation tower;

decantation means for separating condensate from said second distillation tower into an upper layer and a lower layer;

means for recirculating said lower layer from the decantation means to an upper portion of said second distillation tower;

and means for withdrawing from the upper layer of said decantation means a stream consisting of about 32 mol percent tertiary butyl hydroperoxide and about 68 mol percent water as the significant valuable product of the distillation process.

3. The system of claim 2 in which the corrosion-resistant packing consists of a bed of metal particles.

4. The system of claim 2 in which at least one flame arrestor has packing consisting of a bed of particles of alumina.

* * * * *